United States Patent [19]

Cohen

[11] Patent Number: 4,877,890

[45] Date of Patent: Oct. 31, 1989

[54] VITAMIN E INTERMEDIATE

[75] Inventor: Noal Cohen, Montclair, N.J.

[73] Assignee: Hoffmann-La Roche Inc., Nutley, N.J.

[21] Appl. No.: 258,354

[22] Filed: Oct. 17, 1988

Related U.S. Application Data

[62] Division of Ser. No. 58,309, Jun. 5, 1987, Pat. No. 4,801,724.

[51] Int. Cl.$^4$ .......................................... C07D 311/72
[52] U.S. Cl. .................................................... 549/407
[58] Field of Search .......................................... 549/407

[56] References Cited

U.S. PATENT DOCUMENTS 4,789,750  12/1988  Coffen et al. ...................... 549/407

Primary Examiner—Nicky Chan
Attorney, Agent, or Firm—Jon S. Saxe; George M. Gould; William H. Epstein

[57] ABSTRACT

A process for producing alpha-tocopherol and intermediates in this process.

4 Claims, No Drawings

VITAMIN E INTERMEDIATE

This is a division of application Ser. No. 07/058,309 filed June 5, 1988, now U.S. Pat. No. 4,801,724.

CROSS REFERENCE TO RELATED APPLICATION

This application is related to U.S. patent application Ser. No. 07/030,798 filed Mar. 27, 1987, now U.S. Pat. No. 4,789,750.

SUMMARY OF THE INVENTION

This invention provides a novel synthesis for vitamin E which has the structure

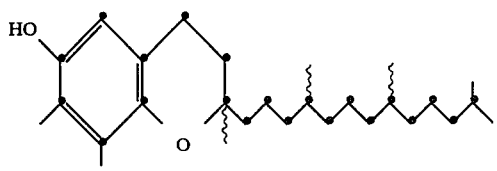

through the reaction in the presence of a palladium containing catalyst, of a compound of the formula:

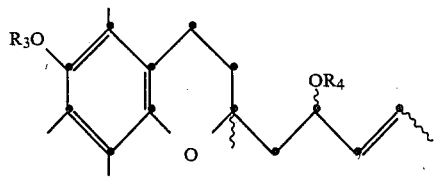

wherein $R_4$ taken together with its attached oxygen atom forms an ester group; and $R_3$ forms an ether hydroxy protecting group with a compound of the formula:

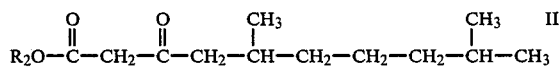

wherein $R_2$ is lower alkyl.

The process of this invention can be utilized to produce the compound I in any of its stereo configurations including naturally occurring optically active vitamin E which has the formula

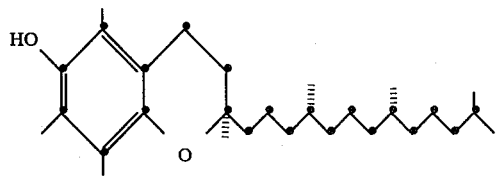

In producing the compound of formula IA, the reactions set forth above are carried out with the optically active forms of the compound of formulas II and III as follows:

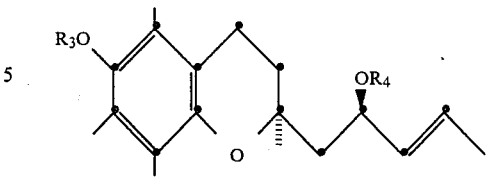

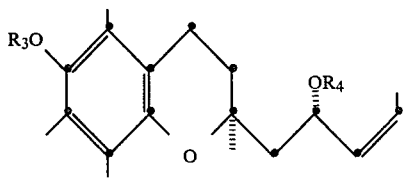

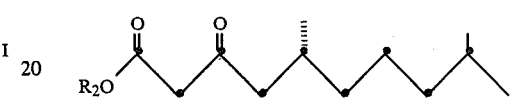

wherein $R_2$, $R_3$ and $R_4$ are as above.

DETAILED DESCRIPTION

As used throughout this application, the term "lower alkyl" includes both straight chain and branched chain alkyl groups having from 1 to 7 carbon atoms such as methyl and ethyl. As used herein, the term "lower alkoxy" denotes lower alkoxy groups containing preferably 1 to 7 carbon atoms, such as methoxy, ethoxy, i-propoxy, t-butoxy, etc. As also used herein, the term "lower alkanoic acid" comprehends an alkanoic acid of from 1 to 7 carbon atoms such as formic acid and acetic acid. The term "lower alkanoyl" designates the monovalent radical formed from a lower alkanoic acid by removal of the OH group on the COOH moiety. Among the preferred lower alkanoyl groups are acetyl, pivaloyl, butyryl, propionyl with acetyl being especially preferred. As further used herein, the term "halogen" or "halo", unless otherwise stated, comprehends all halogens such as fluorine, chlorine, bromine and iodine. Alkali metal includes all alkali metals such as lithium, sodium and potassium.

In the pictorial representation of the compounds given throughout this application, a thickened taper line (▼) indicates a substituent which is in the beta-orientation (in front of the plane of the molecule), a broken line (≡) indicates a substituent which is in the alpha-orientation (behind the plane of the molecule) and a wavy line (ᔥ) indicates a substituent which is in either the alpha- or beta-orientation or mixtures of these isomers. It is to be understood that the pictorial representations of the compounds given throughout the specification are set forth for convenience and are to be construed as inclusive of other forms including enantiomers and racemates and are not to be construed as limited to the particular form shown.

As also used herein, the term "aryl" signifies mononuclear aromatic hydrocarbon groups such as phenyl, which can be unsubstituted or substituted in one or more positions with a lower alkylenedioxy, nitro, halo, or lower alkyl or a lower alkoxy substituent, and polynuclear aryl groups such as naphthyl, anthryl, phenanthryl, etc., which can be unsubstituted or substituted with one or more of the aforementioned groups. The preferred aryl groups are the substituted and unsubstituted mononuclear aryl groups, particularly phenyl.

The term "ether hydroxy protecting group" designates any ether group for protecting a hydroxy group which, upon acid catalyzed cleavage or hydrogenolysis yields the free hydroxy group. Suitable ether protecting groups are, for example, the tetrahydropyranyl, benzyl, t-butyl or 4-methoxy-tetrahydropyranyl ethers. Others are arylmethyl ethers such as benzhydryl, or trityl ethers or alpha-lower alkoxy lower alkyl ether, for example, methoxymethyl or tri(lower alkyl)silyl ethers such as trimethylsilyl ether diethyl-t-butylsilyl ether or dimethyl-tert-butylsilyl ether. Acid catalyzed cleavage is carried out by treatment with an organic or inorganic acid. Among the preferred inorganic acids are the mineral acids such as sulfuric acid, hydrohalic acid, etc. Among the preferred organic acids are lower alkanoic acids such as acetic acid, or sulfonic acids such as paratoluenesulfonic acid, etc. The acid catalyzed cleavage can be carried out in an aqueous medium or in an organic solvent medium. Where an organic acid or alcohol is utilized, the organic acid or alcohol can be the solvent medium. In the case of tetrahydropyranyl ethers, the cleavage is generally carried out in an aqueous medium. In carrying out such cleavage, temperature and pressure are not critical and this reaction can be carried out at room temperature and atmospheric pressure.

The term "ester group" denotes those esters is commonly used to protect hydroxy groups, which can be removed to liberate the hydroxy group by hydrolysis. Among the preferred esters formed by $R_4$ are those esters formed by reacting the hydroxy group with a lower alkanoic acid containing from 1 to 7 carbon atoms present as acetic acid, propionic acid, butyric acid, as well as aroic acids such as benzoic acid and carbonic acid chlorides of the formula

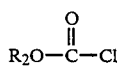

wherein $R_2$ is lower alkyl or aryl as well as lower alkoxy-lower alkanoic acids where the lower alkoxy is as above and the lower alkanoic acids contain from 2 to 7 carbon atoms.

The compound of formula II is reacted with the compound of formula III to produce a compound of the formula:

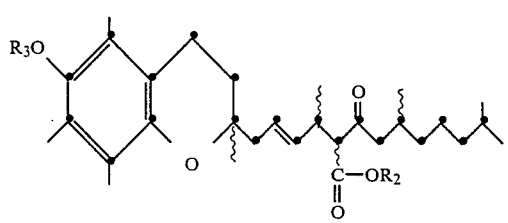

wherein $R_3$ and $R_2$ are as above.

In providing the natural tocopherol of formula I-A either one of the isomeric forms of the compound of formula II i.e. the compound of formula II-A or II-B, can be reacted with the compound of formula III-A to produce a compound of the formula

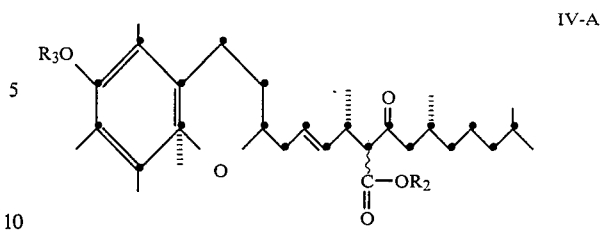

wherein $R_3$ and $R_2$ are as above.

The above condensation to produce the compound of formula IV or any of the stereoisomers thereof is carried out in an organic solvent medium in the presence of a base and a catalyst which is an organic complex of zero valent palladium. Among the preferred catalysts are those complexes of palladium with tri(alkyl or aryl) phosphines. Among the particularly preferred catalysts for use in this reaction are palladium tetrakis(triarylphosphines).

In carrying out the above condensation reaction with a palladium complex as a catalyst, an organic solvent medium is utilized and the reaction proceeds at temperatures of from −90° C. to +25° C., with temperatures of from about −78° to −20° C. being preferred. Furthermore, the reaction is carried out in the presence of a strong base used to convert compound III to its salts. Any strong base can be utilized, such as the alkali metal lower alkoxides, alkali metal hydrides or lower alkyl alkali metals. In carrying out this reaction, any conventional inert organic solvent can be utilized as the reaction medium. Among the preferred solvents are organic ethers and those organic solvents which are liquid at the reaction temperature utilized.

The compound of formula IV is converted to the compound of formula I or its various stereoisomers such as to compounds of formula I-A depending upon the stereoconfiguration of the methyl groups designated by the wavy line in the compound of formula IV via the following intermediates:

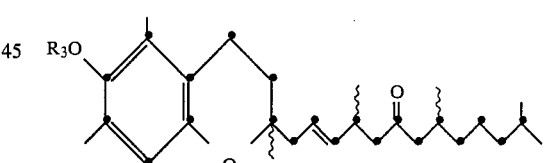

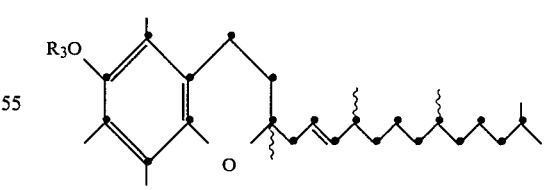

wherein $R_3$ is as above.

The compound of formula IV is converted to the compound of V by ester hydrolysis. This ester hydrolysis causes decarboxylation of the compound of formula IV. Any of the conditions conventional in ester hydrolysis can be utilized to carry out this conversion. The compound of formula V is converted to the compound of formula VI by treating the compound of formula V with hydrazine and alkali metal hydroxide in accordance with standard conditions for a Wolff-Kishner reaction. The compound of formula VI is converted directly to the compound of formula I or its various stereoisomers, such as the compound of formula I-A by hydrogenation utilizing a conventional hydrogenation catalyst, such as platinum or palladium on carbon. Any of the conditions conventional for such hydrogenations can be utilized in this conversion. Where $R_3$ is an ether removable by hydrolysis rather than hydrogenolysis, the ether group is removed by ether hydrolysis after hydrogenation.

On the other hand the compound of formula IV can be converted to the compound of formula I or its various stereoisomeric forms by hydrogenation to form a compound of the formula

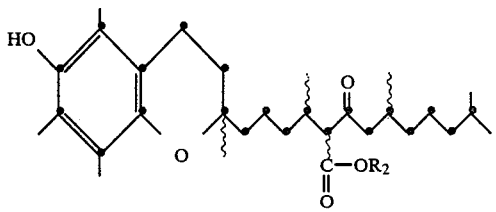

wherein $R_2$ is as above.

Hydrogenation of the compound of formula IV can be accomplished is the manner described is connection with the conversion of the compound of formula VI to the compound of formula I.

The compound of formula VII is next converted to a compound of the formula:

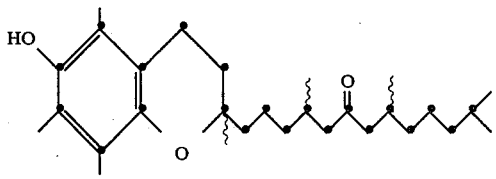

by ester hydrolysis which causes decarboxylation of the compound of formula VII. The ester hydrolysis is carried out in the same manner as described in connection with the formation of a compound of formula V from a compound of formula IV.

The compound of formula VIII can be directly converted to the compound of formula I or any of its desired steroisomeric forms by utilizing a standard Wolff-Kishner reaction such as described in connection with the formation of a compound of formula VI.

The compound of formula III is produced from a compound of the formula

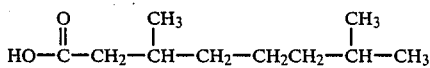

via the following intermediates

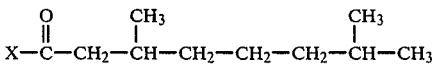

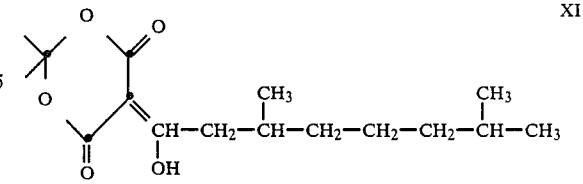

wherein X is halogen.

The compound of formula IX is converted to the compound of formula X having the same stereoconfiguration as the compound of formula X by halogenation. Any conventional method of converting an organic acid to the corresponding acid halide can be utilized in this conversion. The compound of formula X is converted to the compound of formula XI by reacting the compound of formula X with Meldrum's acid according to conventional procedures such as disclosed by Oikawa, Sugano, et al., *J. Org. Chem.*, 1978, 43 2087; and Davidson, and Bernhardt, *J. Am. Chem. Soc.*, 1948, 70 3426.

The compound of formula XI can be converted to the compound of formula III, III-A or III-B, depending upon the stereo configuration of the compound of formula XI, by refluxing the compound of formula XI with a lower alkanol. The particular lower alkanol that is utilized becomes the lower alkyl substituent $R_2$ in the compound of formula III.

The invention is further illustrated by the following examples.

EXAMPLE 1

A solution of 11.37 g (66.1 mmoles) of (R)-(+)-3,7-dimethyloctanoic acid in 50 ml of benzene was stirred while 10 ml (114.6 mmoles) of oxalyl chloride was added. The solution was stirred and refluxed overnight then concentrated in vacuo giving 12.03 g (95.6%) of (R)-(+)-3,7-dimethyloctanoyl chloride as an oil. An 8.2 g (43.0 mmoles) sample of this material in 10 ml of dichloromethane was added to a stirred solution of 6.2 (43.0 mmoles) of Meldrum's Acid and 8.68 ml of pyridine in 40 ml of dichloromethane, at 0° C. The resulting solution was stirred overnight then treated with cold 3N aqueous HCl. The organic phase was separated and the aqueous phase was extracted with dichloromethane. The dichloromethane extracts were combined, dried (Na$_2$SO$_4$), and concentrated in vacuo giving 12.1 g of crude product. This material was dissolved in 100 ml of methanol and the solution was refluxed for 4 hr then cooled and concentrated in vacuo. The residue was chromatographed on silica gel giving (R)-5,9-dimethyl-3-oxodecanoic acid methyl ester as an oil, eluted with pet. ether-ether mixtures.

EXAMPLE 2

A mixture of 1.45 g (3.83 mmoles) of (2S,2R*S*)-1-(3,4-dihydro-6-benzyloxy-2,5,7,8-tetramethyl-2H-benzopyran-2-yl)-3-pentyn-2-ol, 0.25 of Lindlar catalyst, 0.1 ml of quinoline, and 100 ml of 2:1 parts by volume of an ethyl acetate-hexane mixture was stirred at room temperature, under 30 p.s.i. of hydrogen, until gas uptake ceased (ca. 1.5 hr). The catalyst was removed by filtration and the filtrate was concentrated in vacuo. The residue was dissolved in 20 ml of dichloromethane and 0.61 g (4.97 mmoles) of 4-dimethylaminopyridine was added followed by 0.46 ml (4.59 mmoles) of acetic anhydride added dropwise, with stirring. The solution was stirred for 1.5 hr then treated with cold 1N HCl. the mixture was extracted three times with dichloromethane. The extracts were combined, dried (MgSO4), filtered, and concentrated in vacuo. The oily residue was chromatographed on 150 g of silica gel. Elution with pet. ether-ether mixtures afforded 1.6 g of acetic acid (2S,2R*S*,3Z)-1-(3,4-dihydro-6-benzyloxy-2,5,7,8-tetramethyl-2H-1-benzopyran-2-yl)-3-penten-2-yl ester as an oil.

EXAMPLE 3

A 48 mg (1 mmol) sample of a 50% sodium hydride-mineral oil dispersion was washed free of oil with hexane and treated with 5 ml of dry tetrahydrofuran. A solution of 228 mg (1 mmol) of (R)-5,9-dimethyl-3-oxodecanoic acid methyl ester in 5 ml of dry tetrahydrofuran was added dropwise and the mixture was stirred for 20 min then added to a solution of 115.6 mg (0.1 mmol) of tetrakistriphenylphosphine-palladium, and 423 mg (1 mmol) of acetic acid (2S,2R*S*,3Z)-1-(3,4-dihydro-6-benzyloxy-2,5,7,8-tetramethyl-2H-1-benzopyran-2yl)-3-penten-2-yl ester in 10 ml of dry tetrahydrofuran. The mixture was stirred for 1 day at room temperature and 1 day at 50° C. then treated with saturated aqueous sodium bicarbonate and extracted three times with ether. The ether extracts were combined, washed with brine, dried (MgSO4), filtered and concentrated in vacuo. Chromatography of the residue on silica gel, eluting with heptane-ethyl acetate mixtures gave 343 mg (58%) of 2RS-[5-(3,4-dihydro-6-benzyloxy-2,5,7,8-tetramethyl-2H-1-benzopyran-2S-yl)-3E-penten-2S-yl]-3-oxo-5R,9-dimethyldecanoic acid methyl ester as an oil.

EXAMPLE 4

A solution of 343 mg (0.58 mmol) of the product from Example 3 in 10 ml of tetrahydrofuran was treated with 0.5 g of sodium hydroxide. The mixture was stirred and refluxed overnight. An additional 0.5 g of sodium hydroxide, 3 ml of water and 5 ml of methanol were added and refluxing was continued for 1 hr. The mixture was diluted with water and extracted with ether. The ether extracts were dried, filtered, and concentrated in vacuo giving 0.3 g of (2R,4'RS,8'R,2'E)-6-benzyloxy-3,4-dihydro-2,5,7,8-tetramethyl-2-(4',8',12'-trimethyl-6'-oxo-2'-tridecen-1'-yl)-2H-1-benzopyran as an oil.

EXAMPLE 5

The product from Example 4 (300 mg; 0.56 mmol), 31.7 mg (0.56 mmol) of potassium hydroxide, and 70.8 mg (1.41 mmol) of hydrazine hydrate, in 0.6 ml of diethylene glycol was stirred at 200 C. for 4 hr then cooled and treated with 1N HCl. The crude product was isolated by ether extraction. Chromatography on silica gel gave (2R,4'RS,8'R,2'E)-6-benzyloxy-3,4-dihydro-2,5,7,8-tetramethyl-2-(4',8',12'-trimethyl-2'-tridecen-1'-yl)-2H-1-benzopyran as an oil.

EXAMPLE 6

The product from Example 5 is hydrogerated in 5 ml of ethyl acetate over 25 mg of 10% by weight palladium on carbon until gas uptake ceases. The catalyst is filtered and the filtrate is concentrated in vacuo giving (2R,4'RS,8'R)-alpha-tocopherol as an oil.

I claim:
1. A compound of the formula:

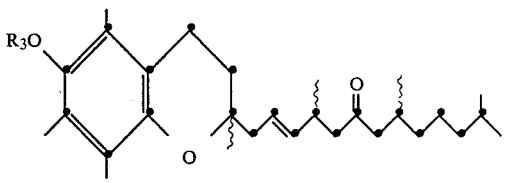

wherein R3 forms an ether hydroxy protecting group.
2. The compound of claim 1 wherein the methyl substituents represented by the wavey line have an alpha orientation.
3. The compound of claim 1 wherein R3 is benzyl.
4. A compound of the formula

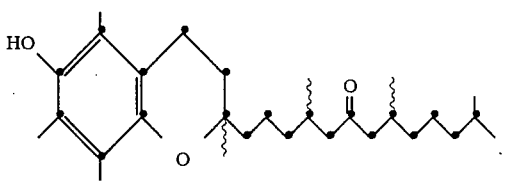

* * * * *